US012376992B2

(12) United States Patent
Brückner et al.

(10) Patent No.: US 12,376,992 B2
(45) Date of Patent: Aug. 5, 2025

(54) OPHTHALMOLOGICAL LASER THERAPY SYSTEM WITH LIGHTING ASSEMBLY

(71) Applicant: Carl Zeiss Meditec AG, Jena (DE)

(72) Inventors: Frank Brückner, Jena (DE); Burkhard Wagner, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 407 days.

(21) Appl. No.: 17/640,638

(22) PCT Filed: Sep. 8, 2020

(86) PCT No.: PCT/EP2020/075038
§ 371 (c)(1),
(2) Date: Mar. 4, 2022

(87) PCT Pub. No.: WO2021/048102
PCT Pub. Date: Mar. 18, 2021

(65) Prior Publication Data
US 2022/0409429 A1    Dec. 29, 2022

(30) Foreign Application Priority Data
Sep. 10, 2019   (DE) ............... 10 2019 213 693.1

(51) Int. Cl.
*A61F 9/008*   (2006.01)

(52) U.S. Cl.
CPC ................... *A61F 9/008* (2013.01)

(58) Field of Classification Search
CPC .............. A61F 9/008; A61N 5/0613; A61N 2005/0652; A61N 2005/0663; A61N 2005/0664; A61N 5/0618
See application file for complete search history.

(56) References Cited

U.S. PATENT DOCUMENTS

| 2002/0040218 A1* | 4/2002 | Fujieda ............... A61F 9/00821 |
| | | 351/200 |
| 2010/0060726 A1* | 3/2010 | Kryger Nielsen ... H05B 47/155 |
| | | 315/294 |
| 2018/0250090 A1* | 9/2018 | Patton ................ A61F 9/00781 |

FOREIGN PATENT DOCUMENTS

| DE | 60116019 T2 | 6/2006 |
| DE | 102015217847 | 3/2017 |
| EP | 1192919 A2 | 4/2002 |

OTHER PUBLICATIONS

International Search Report for PCT/EP2020/075038, mailed Nov. 11, 2020, 3 pages.

(Continued)

*Primary Examiner* — Gary Jackson
*Assistant Examiner* — Sebastian X Lukjan
(74) *Attorney, Agent, or Firm* — DeWitt LLP (57) ABSTRACT

An ophthalmological laser therapy system including an apparatus main body and a laser device which is arranged in the apparatus main body and in a laser arm. The laser arm is arranged on the apparatus main body and includes a lighting arrangement. The invention furthermore relates to a planning device and a planning method for planning a laser therapy on an ophthalmological laser therapy system. It seeks to provide an ophthalmological laser therapy system and a method, by which an optimal psychological (calming) effect can be facilitated for every patient. This calming effect is achieved by an ophthalmological laser therapy system whose laser arm has a lighting arrangement the color of which is variable on an individual basis, and by a corresponding planning device and a corresponding planning method.

20 Claims, 2 Drawing Sheets

(56) References Cited

OTHER PUBLICATIONS

English translation of International Search Report for PCT/EP2020/075038, mailed Nov. 11, 2020, 2 pages.
International Preliminary Report on Patentbility for PCT/EP2020/075038, mailed Mar. 4, 2022, 8 pages.

* cited by examiner

OPHTHALMOLOGICAL LASER THERAPY SYSTEM WITH LIGHTING ASSEMBLY

RELATED APPLICATIONS

This application is a National Phase entry of PCT Application No. PCT/EP2020/075038 filed Sep. 8, 2020, which application claims the benefit of priority to DE Application No. 10 2019 213 98.2 filed Sep. 10, 2019, and DE Application No. 10 2019 213 693.1, filed Sep. 10, 2019, the entire disclosures of which are incorporated herein by reference.

TECHNICAL FIELD

The present invention relates to an ophthalmological laser therapy system comprising an apparatus main body and a laser device which is arranged in the apparatus main body and in a laser arm, the laser arm being arranged on the apparatus main body and comprising a lighting arrangement. The invention furthermore relates to a planning device and a planning method for planning a laser therapy on an ophthalmological laser therapy system.

BACKGROUND

Refractive and therapeutic laser eye surgery is a widespread and established method, which has already been carried out millions of times. Nevertheless, it represents a surgical intervention on the patient, for whom it is an extraordinary situation, and it leads to nervousness and uncertainty immediately before and during the treatment in most patients. In this case, the nervousness is amplified by the approach, required by the method, of the apparatus arm (contact element in the case of fs, smoke extraction in the case of excimer) to the head of the patient (claustrophobic effect). In particular, this nervousness during the laser eye procedure may lead to a premature detachment of the eye from the laser apparatus or the patient does not fixate their eye reliably, this representing a risk to the success of the treatment. Measures for calming and eliciting cooperation from the patient are therefore very important.

One of these measures as a virtual "sky" for the patient in the lying position, when parts of the laser system are just above them and therefore cover the majority of their visual field. The prior art in this respect is a patient surround that is permanently illuminated blue during the preparation and implementation of the laser therapy on the patient's eye, said patient surround being situated on the lower side of the laser arm, for example of the "VisuMax" ophthalmological laser therapy system from the applicant. The assumption made here is that the color blue is generally not perceived as threatening and not perceived as harassing.

However, the physiological effect of colors on different persons varies and a color which tends to calm one person may have a rather unsettling effect on another person. This is probably due to both individual and cultural influences.

SUMMARY OF THE INVENTION

Example embodiments of the present invention provide an ophthalmological laser therapy system and a method, by use of which an optimal psychological (calming) effect can be ensured for every patient.

An ophthalmological laser therapy system comprises an apparatus main body and a laser device which contains a laser source and a first laser therapy optical unit in the apparatus main body and a second laser therapy optical unit and a laser exit opening in a laser arm. The laser arm is arranged on the apparatus main body.

A pulsed laser may be used in this case. The use of a femtosecond laser, whose emitted laser beam is guided through the laser therapy optical unit and focused in tissue in the eye to be processed, is particularly advantageous. At the focus of the laser beam, this leads to separation of the tissue by application of photodisruption. To this end, the patient and in particular the patient's eye to be treated is placed under the laser exit opening of the laser arm and is finally fixated in relation to this laser exit opening by use of a contact glass or a so-called patient interface.

The structure of the laser therapy system usually furthermore contains a scanner system which serves to displace the focus of the laser beam within the tissue to be treated, for example in all three spatial directions, in order thereby to "trace" a processing pattern and finally generate a desired structure. If a laser therapy system is used for a refractive correction in the cornea of the patient's eye, this procedure usually takes several 10 seconds. The fastest laser therapy systems generate the "incisions" required to this end (by way of a local separation of the tissue by application of photodisruption) within approximately 5 seconds. The patient should be made to feel fully at ease during this treatment time, and also already during the preparation time and during the "docking" to the laser exit opening of the laser arm by application of the contact glass or the patient interface.

To this end, the laser arm has a lighting arrangement on its outside, that is to say on an outer side of the laser arm. This lighting arrangement is for example arranged in such a way that the patient can directly feel its effect, that is to say for example on the lower side of the laser arm, with the lighting arrangement in this case being able to extend over the entire lower side or else extend over only a part of the lower side of the laser arm. The color of the lighting arrangement is variable on an individual basis.

According to an example embodiment, the lighting arrangement is formed as a self-luminous partial surface of the laser arm, which achieves the desired color effect directly over the patient.

In contrast to the prior art, it is consequently possible according to the invention to vary the color of an illuminated patient surround for an individual patient. This solves the problem of the different psychological color effect on different patients, and takes care of an optimal psychological and emotional state of each patient before and during the laser treatment. In turn, this minimizes the treatment risk since a patient in an optimal psychological and emotional state is generally prepared to cooperate without qualification and exhibits no panic or defensive reaction.

In an example embodiment of the ophthalmological laser therapy system according to the invention, the laser arm is arranged on the apparatus main body so as to be pivotable about an axis, for example a horizontal axis. As a result, there initially is sufficient space to comfortably position the patient on a patient couch, for example, but the laser arm can be brought close to the patient's eye for treatment purposes.

In the case of a pivotable laser arm, the laser arm comes ever closer to the patient once the latter has been positioned on the patient couch and therefore the laser arm appears more threatening, the closer it is brought to the patient. Such a self-luminous partial surface with a color that is variable on an individual basis is expedient in this case in particular.

In a further embodiment of the ophthalmological laser therapy system according to the invention, the lighting arrangement is part of a fixed patient surround lighting or is arranged in addition to the fixed patient surround lighting. Thus, the ophthalmological laser therapy system may still have further light sources or lighting units. In this case, the lighting arrangement takes account of this general patient surround lighting when implementing the individual color scheme.

In this case, it is very advantageous if, in the ophthalmological laser therapy system according to the invention, the lighting arrangement whose color is variable on an individual basis is configured to be capable of being deactivated and/or variable in terms of brightness of the lighting.

Hence, the color or the brightness of the patient surround can be chosen or varied for an individual patient such that it exhibits the optimal psychological and emotional effect on the patient, or the effect of this lighting arrangement that is individually variable in terms of color can also be eliminated when necessary.

In an advantageous configuration of the ophthalmological laser therapy system according to the invention, the lighting arrangement has at least one of the following adjustment options for its individual variability:
  adjustment by the operator, for example at any time during the workflow,
  adjustment by the patient, for example at any time during the workflow,
  adjustment by the choice of a color from a preset color palette,
  adjustment by the input of RGB values,
  automatic adjustment on the basis of selected planning data or measurable patient data,
  adjustment according to the color scheme and/or the branding of the operating clinic.

By way of example, in the lead up to the treatment, the operator can ask each patient about their preferred color or determine their preferred color by indirect psychological tests, and can set said color on the apparatus as requested. However, the setting may optionally also be varied during the treatment.

Where desired, the patient can determine that setting themselves by use of suitable options, for example in acoustic fashion or by way of a cognitive link of the lighting arrangement to the patient.

It is also possible in one configuration of the lighting arrangement to vary the latter in terms of its color and brightness on the basis of patient data (such as the blood pressure or the pulse of the patient) that are able to be checked during the laser therapy.

In a simple embodiment of the ophthalmological laser therapy system according to the invention, the number of discrete selectable colors of the lighting arrangement from a preset color palette is greater than or equal to two.

In an advantageous ophthalmological laser therapy system according to the invention, the color of the lighting arrangement can be varied continuously within the range of visible light. This offers the best possible adaptation to the optimal individual color scheme for the patient.

In a further variant of the ophthalmological laser therapy system according to the invention, the latter contains other lighting elements, which are likewise variable and have the same or a different color to the patient surround lighting, in addition to the lighting arrangement. In this case, too, the lighting arrangement takes account of these lighting elements when implementing the individual color scheme, optionally in a chronological sequence if these additional lighting elements are not continuously in operation.

A planning device according to the invention for planning a laser therapy on an ophthalmological laser therapy system is configured to determine, for an individual patient, a color to be set for a lighting arrangement on a laser arm of the ophthalmological laser therapy system.

Such a planning device may be part of a control device in the interior of the ophthalmological laser therapy system, which controls all components of this ophthalmological laser therapy system and which, in turn, may be configured in one piece or in many pieces. However, the planning device may also be an external planning device, which is used to plan a sequence on an ophthalmological laser therapy system in advance.

A planning method according to the invention for planning a laser therapy on an ophthalmological laser therapy system, within the scope of which a color to be set for a lighting arrangement on the laser therapy system is determined for an individual patient and is subsequently set, for example in automated fashion.

This determination of the color scheme for an individual patient can be implemented on the basis of one or more of the above-described special features, that is to say for example:
  implementing advance planning of the setting of the individual color scheme by way of a prior choice of a color from a preset color palette and/or by way of the input of RGB values;
  containing intervention options for the operator, for example at any time during the workflow;
  containing intervention options for the patient, for example at any time during the workflow;
  containing an automatic adjustment and readjustment of the individual color scheme on the basis of selected planning data or measurable patient data;
  considering the color scheme and/or the branding of the operating clinic;
  considering a patient surround lighting and/or further lighting elements of different colors.

Thus, the planning device according to the invention and the planning method according to the invention determine—in addition to the laser parameters such as intensity of the laser pulses and their relative position—a color fitting to the respective patient for illumination purposes.

The present invention will now be explained on the basis of example embodiments.

DETAILED DESCRIPTION

Figure 1A:
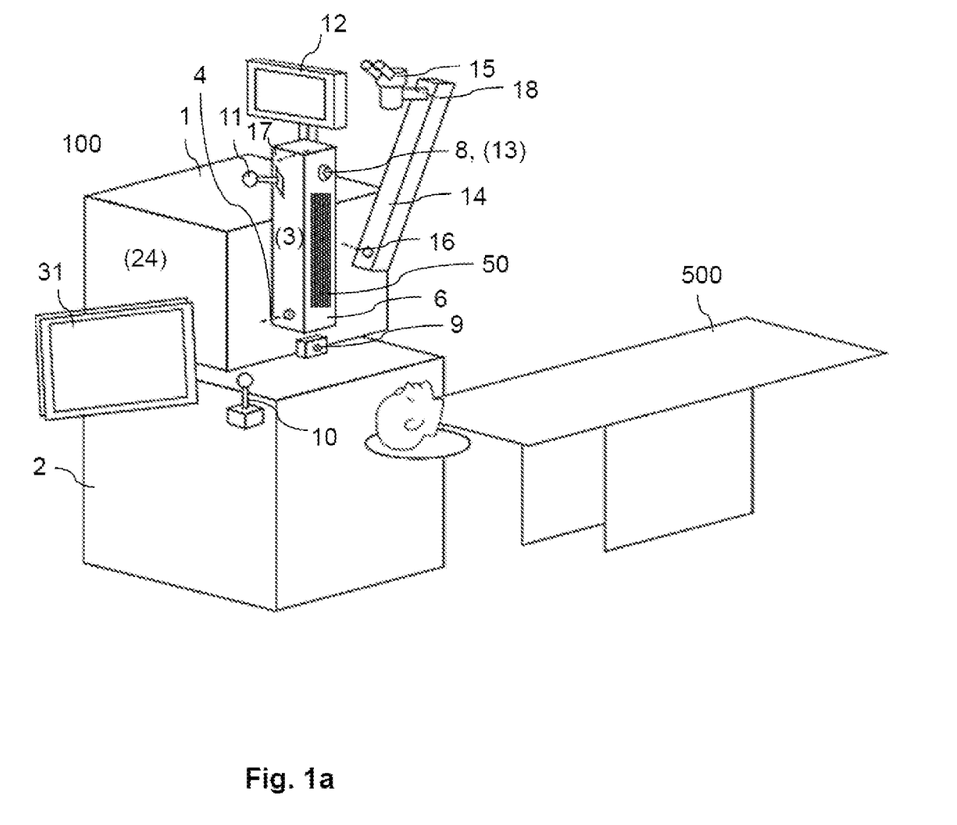
FIGS. 1a and 1b depict an example embodiment of an ophthalmological laser therapy system.
Figure 1B:
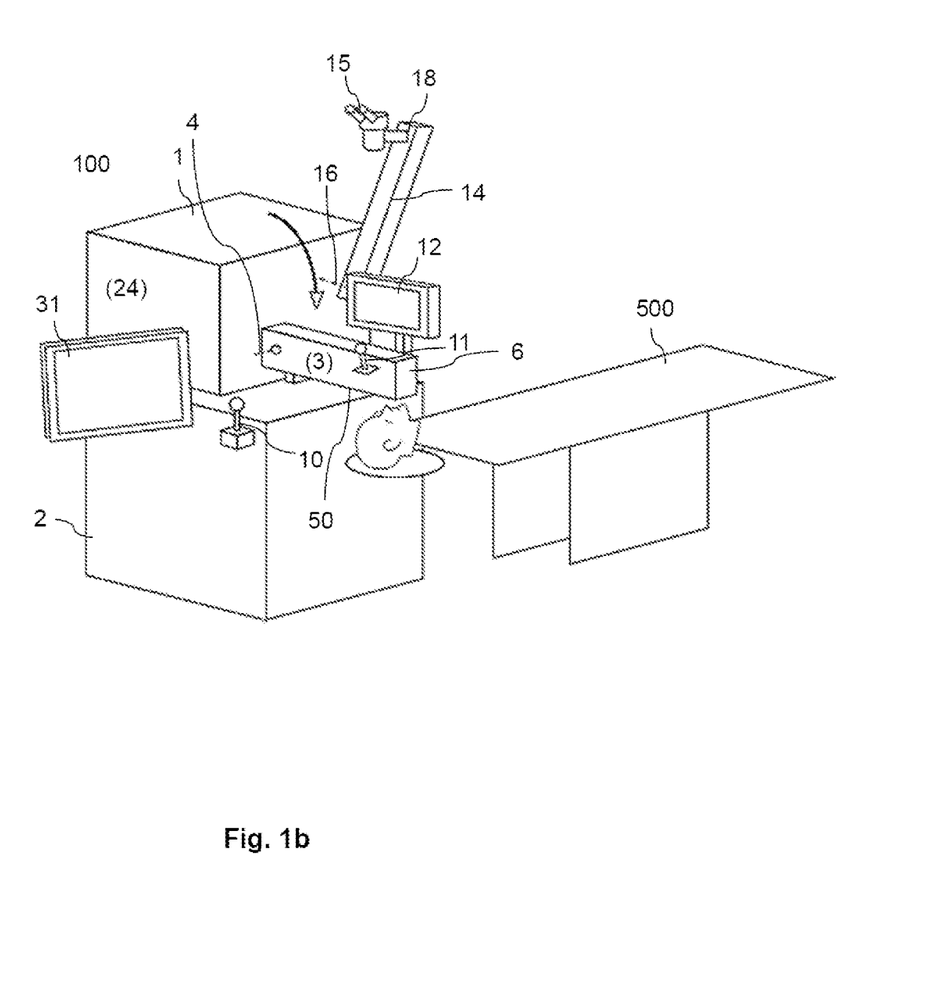

FIGS. 1a and 1b described an example embodiment of an ophthalmological laser therapy system 100 in more detail. It attains a correction of the visual acuity of a patient's eye by application of a laser, for example by use of a pulsed and focused femtosecond laser beam, whose focal point is scanned through tissue within the eye and which thereby separates this tissue within the eye, in particular within the cornea and/or the lens of the patient's eye. By way of example, the refractive error can be corrected by separating a narrow lenticule in the cornea and subsequently extracting the lenticule via a small opening in the cornea.

The ophthalmological laser therapy system 100 of FIGS. 1a and 1b is distinguished by a laser pivot arm 3 that is fastened to the apparatus head 1 in a manner pivotable about a horizontal axis 4 and that can be pivoted back and forth between a rest position and a work position. Since this laser pivot arm 3 is pivoted over the patient for laser therapy on the patient's eye but can be returned into a rest position for steps in which the laser pivot arm 3 is not required in order to use the space above the work position differently, the laser pivot arm 3 is protected by virtue of the laser pivot arm 3 being enclosed by a pivot arm housing 6, which is fastened in a pivotable manner to the apparatus head 1 in coaxial fashion in relation to the laser pivot arm 3 ("arm-in-arm principle").

The pivot arm housing 6 has a laser exit opening 8 which is positioned such that, when the laser pivot arm 3 is brought into the work position, said laser exit opening is directed at the eye of a patient to be treated, who can be placed and positioned appropriately on the patient couch 500. A lighting arrangement, in this case a self-luminous partial surface 50, is arranged on a lower side of the laser pivot arm 3, that is to say on the side of the laser pivot arm 3 that in the work position faces the patient. This lighting arrangement 50 can be controlled such that there is an individual color scheme for a patient, which can even still be varied during a laser therapy.

In this case, the ophthalmological laser therapy system 100 is composed of an apparatus base 2 and an apparatus head 1 that is adjustable on this apparatus base 2 in terms of its height above the plane of the floor, that is to say the z-direction, and in terms of its position in the plane, that is to say in the x- and y-directions. Together, apparatus head 1 and apparatus base 2 form the apparatus main body 1, 2. The apparatus head 1 contains a first part of the laser therapy optical unit required for performing the laser therapy. In the example embodiment, the apparatus head 1 also contains the laser source, in this case a femtosecond laser source, required to produce a corresponding pulsed laser beam.

The second part of the laser therapy optical unit is rotatably mounted about a horizontal first axis 4 in a laser pivot arm 3. The laser pivot arm 3 can be pivoted about this first axis 4 from a rest position, which is shown in FIG. 1a and in which it projects upward in approximately perpendicular fashion, into a work position, which is shown in FIG. 1b and in which it is arranged approximately horizontally on the apparatus head 1, i.e., approximately parallel to the plane of the floor, and back again.

If use is furthermore made of a further independent examination pivot arm 14 in addition to the laser pivot arm 3, said examination pivot arm containing a surgical microscope 15 in particular, said examination pivot arm is arranged pivotably about an axis such that all work steps of a laser therapy on the eye of a patient can be carried out in such a way that the point of action of all work steps aided by the laser pivot arm 3 or the examination pivot arm 6 always remains stationary, that is to say the position of the patient's eye need not be changed during the entire laser therapy. The position of the patient's eye in the first work step determines the position of all subsequent work steps and hence the point of action of the devices required in each case, which are on the various pivot arms 3, 14. This is facilitated by a special arrangement 300 of the pivot axes 4, 16 of the various pivot arms 3, 14 in relation to one another on the apparatus head 1 of the ophthalmological laser therapy system 100, wherein the first axis 4 of the laser pivot arm 3 and the second axis 16 of the examination pivot arm 14 have an appropriate arrangement 300 with respect to one another on the apparatus head 1, and, firstly, a therapy visual display unit 12 fastened to the pivot arm housing 6 in movable fashion is coupled to the movement of the pivot arm housing 6 and, secondly, the surgical microscope 15, which is movably fastened to the examination pivot arm 14, is coupled to the movement of the examination pivot arm 14 so that the therapy visual display unit 12 and the surgical microscope 14 always remain without tilt. In principle, the examination pivot arm 14 may also be equipped with a further lighting arrangement 50; however, this is not the case in the example shown since there is a greater distance between arm and patient during the use of the examination pivot arm 14 and so the effect on the patient is substantially less decisive than for the laser pivot arm 3 and, moreover, advantageous light conditions for the operator are the more important requirement for working with the examination pivot arm 14.

In this case, depending on the therapy step, one of the two arms, that is to say either the laser pivot arm 3 or the examination pivot arm 14, is situated so as to be pivoted over the patient in the work position and the other one of the two arms is in the rest position (folded up). While the examination pivot arm—if used—remains at a relatively large distance from the patient, examinations are carried out very quickly as a rule, even a surgical manipulation of the patient's eye under the surgical microscope 15.

In this case, the lighting arrangement 50 is always initiated before pivoting the laser pivot arm 3 into the work position and is only deactivated again after the laser pivot arm 3 has been brought into the rest position.

A typical course of the treatment is now described below, for example as may be implemented for the separation of a lenticule in the cornea of a patient's eye and the subsequent extraction of the lenticule through a narrow opening, using an above-described ophthalmological laser therapy system 100:

First, the treatment or therapy parameters are planned on a planning visual display unit 31, which is likewise arranged directly on the ophthalmological laser therapy system 100 in this example embodiment. However, alternatively, the planning visual display unit 31 may also be spatially separated from the ophthalmological laser therapy system 100. When planning, the ophthalmological laser therapy system 100 is for example in a standby position, that is to say the laser pivot arm 3 and optionally the examination pivot arm 14, too, are pivoted up vertically in the rest position on the system.

The patient is positioned on the patient couch 500. This is possible with some comfort on account of the pivoted-up laser pivot arm 3.

Then, the operator (i.e., the surgeon, operating physician or an assistant) positions the height of the apparatus head 1 by operation of a joystick 10 on this apparatus head 1, by which the translational movement of the apparatus head 1 over the apparatus base 2 can be controlled. In the process, orientation is provided by the image supplied by the camera 9, said image, including an overlaid symbol of a pivoted-down laser pivot arm 3, being visible on the therapy visual display unit 12 and/or on the planning visual display unit 31. As an alternative to the joystick, the positioning can also be effectuated in other embodiments by inputs on one of the two visual display units 12, 31 or by way of push-buttons on the laser therapy system 100.

The operator triggers the motor-driven pivoting-down of the laser pivot arm 3 in, and together with, its pivot arm housing 6; a corresponding push-button utilized to this end is not illustrated in the figures. As a result of the pre-positioning and the still retracted laser exit opening 8 of the laser pivot arm, a clear space remains between the laser exit opening 8 and the patient's eye, said clear space expediently having a size of between 50 mm and 150 mm. Before pivoting down, the self-luminous partial surface 50 on the lower side of the laser 3 is initiated with the determined optimal color scheme for the corresponding patient. As a result, the downward pivot and approach of the laser arm is perceived less uncomfortable by the patient and the then subsequent therapy method is perceived more attentively and in more cooperative fashion by the patient. Moreover, it is possible even during the therapy method to adapt the color scheme on the basis of the behavior and measurable patient data, for example the pulse and/or the blood pressure.

Now, a contact glass is placed on the laser exit opening 8, if this has not yet happened in the rest position of the laser pivot arm 3. The contact glass is held against the laser exit opening 8 by application of negative pressure.

Then, the operator initiates the release of the movement of the laser pivot arm 3 within the pivot arm housing 6 by operation of a joystick rotation of the joystick 11 on the pivot arm housing 6, or alternatively by use of a separate pushbutton (not illustrated). An automatic trigger of the movement by way of the applied contact glass is also possible in other embodiments. The laser exit opening 8 with the contact glass moves toward the eye in the process.

Finally there is the docking phase, that is to say the phase in which the contact glass is affixed: Here, the operator steers the contact glass toward the eye of the patient using the joystick 11 under observation via the video microscope 13. Fixating the eye by suctioning the eye to the contact glass is triggered by a button on the joystick 11 once the correct position has been reached. In one configuration, it is possible to assist the correct positioning or centering of the contact glass or another patient interface on the eye by virtue of processing the video microscope image and using this to control the apparatus head 1.

Hence, it is now finally possible by operation of a foot switch, which is not illustrated here, to start the actual laser therapy step by activating the laser beam, which is guided through the laser therapy optical units and the laser exit opening and focused in the patient's eye.

After completing this laser therapy step, the suctioning of the eye by application of the negative pressure is released by virtue of the pressure being increased here again, the laser pivot arm 3, and hence also the laser exit opening 8, are pivoted back into the pivot arm housing 6 again and the apparatus head 1 is slightly raised by a displacement in the z-direction. Hence, a safe distance from the eye is present once again. The contact glass or the patient interface can be removed from the laser exit opening 8, with the release being effectuated by brief upward pressure.

Now, the laser pivot arm 3 is pivoted up again together with its pivot arm housing 6; the clear space above the patient is re-established. Now, it is possible to perform further work steps or the patient can leave their position on the patient couch 500. At this point the self-luminous partial surface 50 is deactivated again.

However, where both eyes of a patient are to be treated, the apparatus head 1 can be moved by a translational movement in the x- and/or y-direction over the apparatus base 2 prior to pivoting-up of the laser pivot arm 3 with its pivot arm housing 6 in its rest position such that the laser pivot arm 3 with its pivot arm housing 6 is positioned over the other eye. A treatment of the second eye can then be effectuated in the same way by virtue of a new contact glass or patient interface being secured on the laser exit opening 8 by application of negative pressure, and all steps following this are carried out as described above.

Furthermore, an examination pivot arm 14 containing an examination device, in this case a surgical microscope 15, is also fastened in a pivotable manner about a second axis 16 on the apparatus head 1 in this example embodiment of an ophthalmological laser therapy system 100 according to the invention. By way of example, such a surgical microscope is required, or at least suggested, for the second main work step of the "SMILE" treatment. To this end, after pivoting up the laser pivot arm 3 with its pivot arm housing 6 into its rest position after completing the actual laser therapy step, as described here, the treatment is continued as follows:

The operator initiates the motor-driven downward pivoting of the examination pivot arm 14 by pressing a button. The motor moves the examination pivot arm 14 into its work position, where it rests on a stop. The work position is determined by expedient selection of the relative position of the two pivot axes, that is to say the first axis 4 and the second axis 16, and the end position of the examination pivot arm 14 that is determined by the stop is determined in such a way that the eye to be treated further lies in the examination volume of the surgical microscope 15 directly after pivoting down the examination pivot arm 14.

Minor corrections, to the extent that these are necessary, are possible by adjusting the position of the apparatus head 1 in relation to the apparatus base 2 by translational movements. Serving to this end is the joystick 10 present on the apparatus base 2, a separate foot console or a joystick present on the surgical microscope 15.

Once the examination pivot arm 14 with the surgical microscope 15 has been appropriately positioned, the lenticule extraction is carried out by the operator.

After completing the lenticule extraction, the examination pivot arm 14 with the surgical microscope 15 is pivoted up in a motor-driven manner and thereby pivoted back into its rest position. This can be initiated by pressing a button or else—as already described above for the pivot arm housing 6 and the laser pivot arm 3—by pushing. Hence, the clear space over the patient is re-established.

The aforementioned features of the invention, which are explained in various example embodiments, can be used not only in the combinations specified in an example manner but also in other combinations or on their own, without departing from the scope of the present invention.

A description of a piece of equipment relating to method features is analogously applicable to the corresponding method with respect to these features, while method features correspondingly represent functional features of the equipment described.

The invention claimed is:

1. An ophthalmological laser therapy system that facilitates the performance of eye surgical procedures, comprising:
   an apparatus main body structured to define a space to accommodate a patient couch adjacent to the apparatus main body; and
   a laser device which contains a laser source and a first laser therapy optical unit in the apparatus main body and a second laser therapy optical unit and a laser exit opening in a laser arm,
   the laser arm being arranged on the apparatus main body, and
   wherein the laser arm has on an outside thereof, on a bottom side of the laser arm and above the patient couch on which a patient's head is positioned, a lighting arrangement projecting a patient color scheme, a color of which is variable on an individual patient basis and that achieves a desired color effect viewable by the patient when the patient's head is positioned on the patient couch.

2. The ophthalmological laser therapy system according to claim 1, wherein the lighting arrangement further comprises a self-luminous partial surface.

3. The ophthalmological laser therapy system according to claim 1, wherein the laser arm is arranged on the apparatus main body so as to be pivotable about an axis.

4. The ophthalmological laser therapy system according to claim 3, wherein the axis comprises a horizontal axis.

5. The ophthalmological laser therapy system according to claim 1, wherein the lighting arrangement is part of a patient surround lighting or is arranged in addition to the patient surround lighting.

6. The ophthalmological laser therapy system according to claim 1, wherein the lighting arrangement is configured to be capable of being deactivated, variable in terms of brightness of the lighting or both.

7. The ophthalmological laser therapy system according to claim 1, wherein the lighting arrangement has at least one of the following adjustment options for its individual variability:
   adjustment by the operator,
   adjustment by the operator, at any time during workflow,
   adjustment by the patient,
   adjustment by the patient, at any time during workflow,
   adjustment by the choice of a color from a preset color palette,
   adjustment by the input of RGB values,
   automatic adjustment on the basis of selected planning data or measurable patient data, and
   adjustment according to a color scheme, branding of the operating clinic or both.

8. The ophthalmological laser therapy system according to claim 1, wherein a number of discrete selectable colors of the lighting arrangement from a preset color palette is greater than or equal to two.

9. The ophthalmological laser therapy system according to claim 1, wherein the color of the lighting arrangement can be varied continuously within the range of visible light.

10. The ophthalmological laser therapy system according to claim 5, further comprising other lighting elements, which are likewise variable and have the same or a different color as the patient surround lighting.

11. The ophthalmological laser therapy system according to claim 1, further comprising an examination pivot arm wherein the examination pivot arm further comprises a further lighting arrangement.

12. The ophthalmological laser therapy system according to claim 11, wherein the further lighting arrangement further comprises a self-luminous partial surface.

13. The ophthalmological laser therapy system according to claim 11, wherein the further lighting arrangement is configured to be capable of being deactivated, variable in terms of brightness of the lighting or both.

14. The ophthalmological laser therapy system according to claim 11, wherein the further lighting arrangement has at least one of the following adjustment options for its individual variability:
   adjustment by the operator,
   adjustment by the operator, at any time during workflow,
   adjustment by the patient,
   adjustment by the patient, at any time during workflow,
   adjustment by the choice of a color from a preset color palette,
   adjustment by the input of RGB values,
   automatic adjustment on the basis of selected planning data or measurable patient data, and
   adjustment according to a color scheme, branding of the operating clinic or both.

15. The ophthalmological laser therapy system according to claim 11, wherein the color of the further lighting arrangement can be varied continuously within the range of visible light.

16. The ophthalmological laser therapy system according to claim 11, wherein a number of discrete selectable colors of the further lighting arrangement from a preset color palette is greater than or equal to two.

17. The ophthalmological laser therapy system according to claim 11, wherein the lighting arrangement is part of a patient surround lighting or is arranged in addition to the patient surround lighting.

18. A planning device for planning a laser therapy on an ophthalmological laser therapy system that facilitates the performance of eye surgical procedures, comprising:
   a planning visual display unit operably coupled to the ophthalmological laser therapy system comprising a laser arm, wherein the ophthalmological laser therapy system is structured to define a space to accommodate a patient couch adjacent to the ophthalmological laser therapy system;
   wherein the planning visual display unit is configured to determine, for an individual patient, a color to be set for a lighting arrangement on an outside of the laser arm of the ophthalmological laser therapy system, on a bottom side of the laser arm and above the patient couch on which a patient's head is positioned, the color being variable on an individual patient basis and the lighting arrangement displaying a desired color effect viewable by the patient when the patient's head is positioned on the patient couch.

19. A planning method for planning a laser therapy on an ophthalmological laser therapy system, comprising:
   providing the ophthalmological laser therapy system comprising a lighting arrangement and a laser arm, wherein the ophthalmological laser therapy system is structured to define a space to accommodate a patient couch adjacent to the ophthalmological laser therapy system;
   determining, via a planning visual display unit operably coupled to the ophthalmological laser therapy system, a color to be set for the lighting arrangement on an outside of the laser arm on a bottom side of the laser arm and above the patient couch on which a patient's head is positioned, the lighting arrangement projecting a patient color scheme, a color of which is variable on an individual patient basis and that achieves a desired color effect viewable by the patient when the patient's head is positioned on the patient couch of the ophthalmological laser therapy system for an individual patient,
   wherein determining the color comprises at least one step selected from the group of: making a choice of a color from a preset color palette or input of RGB values, making an operator-based intervention, making a patient-based intervention, and making an automatic adjustment or readjustment of the color, wherein the making of the automatic adjustment or readjustment of the color is made on the basis of selected planning data, measurable patient data, a patient surround lighting, or further lighting elements of different colors, and any combination thereof; and
   subsequently, setting the color.

20. The planning method for planning a laser therapy according to claim 19, further comprising setting the color in automated fashion based on measured patient data during therapy with the ophthalmological laser therapy system.

* * * * *

UNITED STATES PATENT AND TRADEMARK OFFICE
CERTIFICATE OF CORRECTION

| | | |
|---|---|---|
| PATENT NO. | : 12,376,992 B2 | Page 1 of 1 |
| APPLICATION NO. | : 17/640638 | |
| DATED | : August 5, 2025 | |
| INVENTOR(S) | : Brückner et al. | |

It is certified that error appears in the above-identified patent and that said Letters Patent is hereby corrected as shown below:

In the Specification

Column 1, Line 38, delete "or the" and insert --if the--

Column 1, Line 42, delete "as a" and insert --is a--

Column 4, Line 64, delete "is distinguished" and insert --are distinguished--

Column 7, Line 4, delete "the then" and insert --the--

Signed and Sealed this
Fourteenth Day of October, 2025

John A. Squires
*Director of the United States Patent and Trademark Office*